(12) United States Patent
Tessier et al.

(10) Patent No.: US 12,141,814 B2
(45) Date of Patent: Nov. 12, 2024

(54) SYSTEMS AND METHODS FOR IMPROVING FOOD SAFETY

(71) Applicant: Honeywell International Inc., Morris Plains, NJ (US)

(72) Inventors: Patrick C. Tessier, Maple Grove, MN (US); Jared Faber, Minneapolis, MN (US); John Cronin, Jericho, VT (US); Michael Baker, Georgia, VT (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 780 days.

(21) Appl. No.: 16/569,380

(22) Filed: Sep. 12, 2019

(65) Prior Publication Data
US 2021/0081956 A1    Mar. 18, 2021

(51) Int. Cl.
| | |
|---|---|
| *G06Q 10/087* | (2023.01) |
| *G01J 5/10* | (2006.01) |
| *G01N 25/56* | (2006.01) |
| *G05B 19/042* | (2006.01) |
| *G06Q 30/018* | (2023.01) |
| *G08B 21/02* | (2006.01) |
| *H04N 7/18* | (2006.01) |

(52) U.S. Cl.
CPC ............ *G06Q 30/018* (2013.01); *G01J 5/10* (2013.01); *G01N 25/56* (2013.01); *G05B 19/042* (2013.01); *G06Q 10/087* (2013.01); *G08B 21/02* (2013.01); *H04N 7/181* (2013.01); *H04N 7/183* (2013.01); *G05B 2219/2614* (2013.01)

(58) Field of Classification Search
CPC ....... G06Q 30/018; G06Q 10/087; G01J 5/10; G01N 25/56; G05B 19/042; G05B 2219/2614; G08B 21/02; H04N 7/181; H04N 7/183

USPC ......................................................... 703/317
See application file for complete search history.

(56) References Cited

U.S. PATENT DOCUMENTS

| | | | |
|---|---|---|---|
| 2009/0051545 A1* | 2/2009 | Koblasz ............... | G08B 21/245 340/573.1 |
| 2012/0150333 A1* | 6/2012 | De Luca ............... | G06V 40/20 700/109 |
| 2014/0241571 A1* | 8/2014 | Bilet .................... | G06T 7/0004 382/103 |
| 2015/0002660 A1* | 1/2015 | Lee ...................... | H04N 23/80 348/135 |
| 2015/0077258 A1* | 3/2015 | Nelson ............... | G06Q 30/0207 705/14.1 |

(Continued)

OTHER PUBLICATIONS

Fakruddin et al., "Predictive Microbiology: Modeling Microbial Responses in Food," Ceylon Journal of Science, 40(2): 11 pages, 2011.

*Primary Examiner* — Naomi J Small
(74) *Attorney, Agent, or Firm* — Seager, Tufte & Wickhem, LLP

(57) ABSTRACT

A video-based food safety compliance system for use in a food area of a building includes a video camera having a field of view that encompasses at least part of the food area, a user interface and a controller that is operably coupled to the video camera and to the user interface. The controller is configured to receive video from the video camera and to analyze the video to determine when one or more food safety compliance rules are violated. The controller outputs an alert in response to determining that one or more of the food safety compliance rules have been violated.

20 Claims, 8 Drawing Sheets

(56) References Cited

U.S. PATENT DOCUMENTS

| | | | |
|---|---|---|---|
| 2015/0310385 A1* | 10/2015 | King | G06Q 10/087 |
| | | | 705/28 |
| 2017/0220985 A1* | 8/2017 | White | H04L 67/566 |
| 2017/0365157 A1* | 12/2017 | Shoari | H04B 17/318 |
| 2018/0147718 A1 | 5/2018 | Oleynik | |
| 2018/0157232 A1 | 6/2018 | Chen | |
| 2018/0165771 A1 | 6/2018 | Lesik et al. | |
| 2018/0285649 A1* | 10/2018 | Shi | G08B 13/19613 |
| 2018/0317690 A1 | 11/2018 | Staton et al. | |
| 2019/0069728 A1* | 3/2019 | Alfarra | A23N 12/02 |
| 2019/0231147 A1 | 8/2019 | Chen et al. | |
| 2019/0293456 A1* | 9/2019 | Brach | A47G 19/027 |
| 2020/0249660 A1* | 8/2020 | Rao | G05B 13/0265 |

* cited by examiner

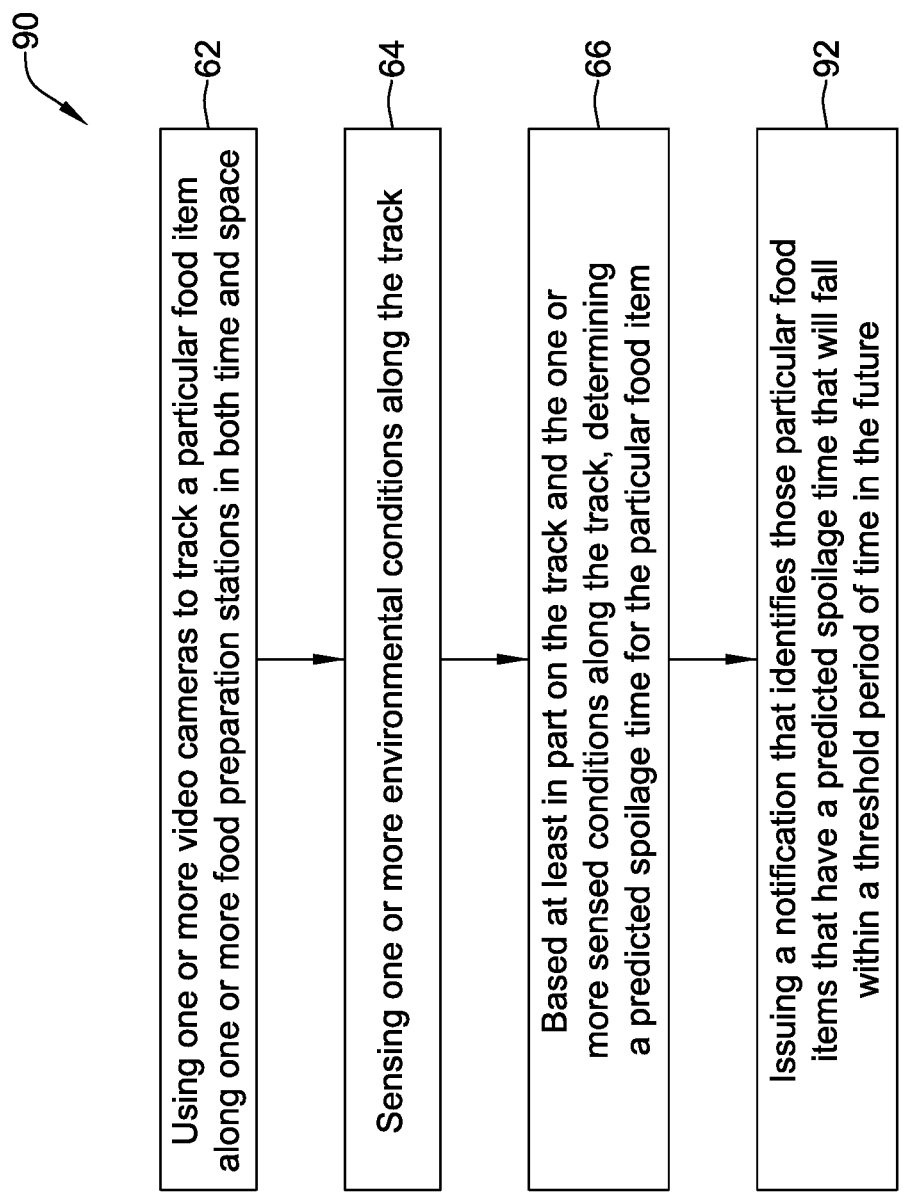

SYSTEMS AND METHODS FOR IMPROVING FOOD SAFETY

TECHNICAL FIELD

The present disclosure relates generally to improving food safety, and more particularly relates to systems, including video-based systems, for evaluating and improving compliance with food safety compliance rules.

BACKGROUND

The transport and handling of food items, from farm to table, is a complex system. Many food items are temperature-sensitive, meaning that refrigeration is a required component of the transport and handling of these food items. Some food items need to be kept under refrigeration while other food items need to be kept frozen in order to maintain the quality and safety of the food items. The needs for thermal and inventory control remain even once food items reach a destination such as but not limited to a grocery store or a restaurant. There are food safety compliance rules that govern how food is to be handled, both with respect to inventory control and thermal control. What would be desirable are methods and systems for improving compliance with food safety rules.

SUMMARY

The present disclosure relates generally to a systems and methods for improving compliance with food safety rules. An example of the disclosure includes a video-based food safety compliance system for use in a food area of a building. The video-based food safety compliance system includes a video camera having a field of view that encompasses at least part of the food area, a user interface and a controller that is operably coupled to the video camera and to the user interface. The controller is configured to receive video from the video camera and to analyze the video to determine when one or more food safety compliance rules are violated. The controller outputs an alert, such as via the user interface, in response to determining that one or more of the food safety compliance rules have been violated.

Another example of the disclosure includes a method for predicting a spoilage time of a particular food item along a food preparation process in a building. The illustrative method includes using one or more video cameras to track a particular food item along one or more food preparation stations in both time and space. One or more environmental conditions are sensed along the track. Based at least in part on the track and the one or more sensed conditions along the track, a predicted spoilage time for the particular food item may be determined.

Another example of the disclosure includes an inventory control system for use in controlling food inventory within a food storage area. The illustrative inventory control system includes a sensor operable to detect a measure of inventory control, a user interface and a controller that is operably coupled to the sensor and to the user interface. The controller is configured to receive the measure of inventory control from the sensor and to track the measure of inventory control over time. The controller is configured to determine if the measure of inventory control over time indicates a violation of inventory control compliance rules. The controller is configured to generate a report describing the instances in which inventory control compliance rules are violated and to output the report via the user interface so that a supervisor can implement improvements in compliance with the inventory control compliance rules.

The preceding summary is provided to facilitate an understanding of some of the innovative features unique to the present disclosure and is not intended to be a full description. A full appreciation of the disclosure can be gained by taking the entire specification, claims, figures, and abstract as a whole.

BRIEF DESCRIPTION OF THE FIGURES

The disclosure may be more completely understood in consideration of the following description of various examples in connection with the accompanying drawings, in which:

FIG. 8 is a flow diagram showing an illustrative method.

Figure 1:
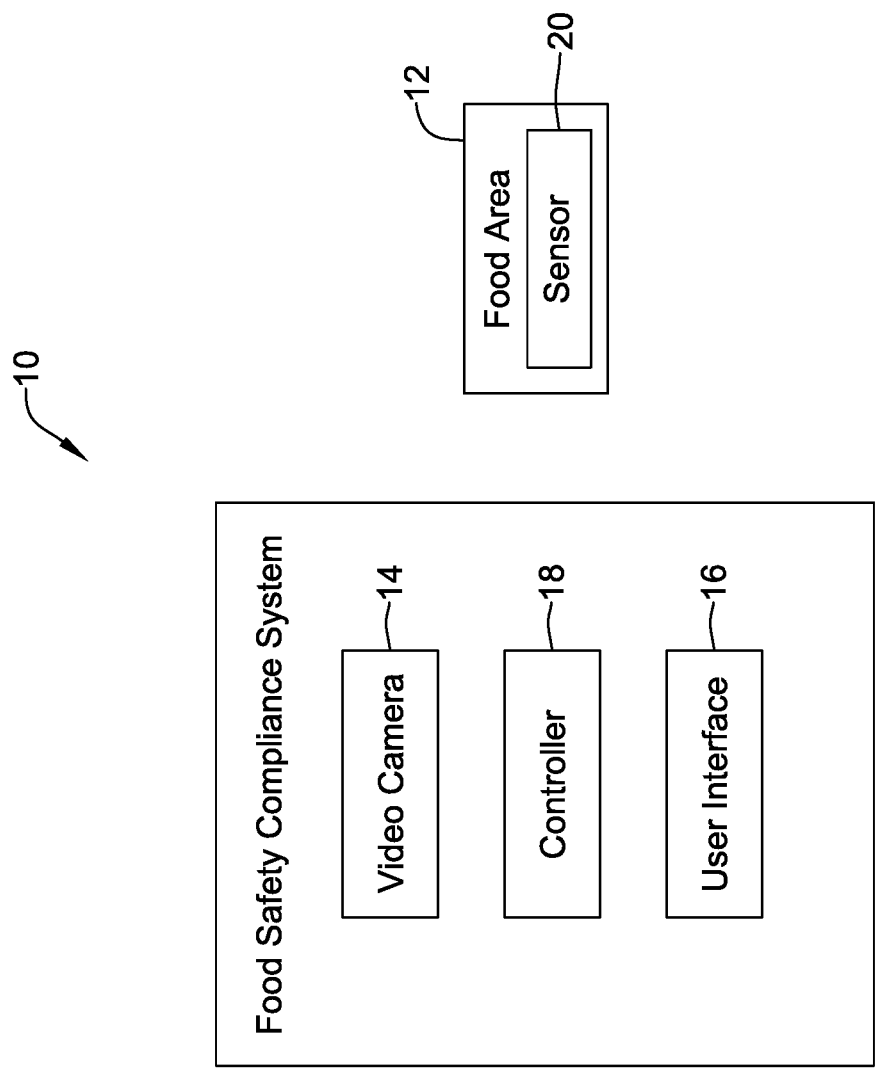
FIG. 1 is a schematic block diagram of an illustrative video-based food safety compliance system.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DESCRIPTION

The following description should be read with reference to the drawings, in which like elements in different drawings are numbered in like fashion. The drawings, which are not necessarily to scale, depict examples that are not intended to limit the scope of the disclosure. Although examples are illustrated for the various elements, those skilled in the art will recognize that many of the examples provided have suitable alternatives that may be utilized.

All numbers are herein assumed to be modified by the term "about", unless the content clearly dictates otherwise. The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic is described in connection with an embodiment, it is contemplated that the feature, structure, or characteristic may be applied to other embodiments whether or not explicitly described unless clearly stated to the contrary.

FIG. 1 is a schematic block diagram of an illustrative video-based food safety compliance system 10 for use in a food area 12 of a building. The illustrative video-based food safety compliance system 10 includes a video camera 14 that may be configured to have a field of view that encompasses at least part of the food area 12. The illustrative video-based food safety compliance system 10 includes a user interface 16 and a controller 18 that is operably coupled to the video camera 14 and to the user interface 16. The controller 18 may, for example, be configured to receive video from the video camera 14 and to analyze the video to determine whether one or more food safety compliance rules have been, or are being, violated. The food safety compliance rules may pertain to the activity or activities occurring within the food area, and may pertain to how inventory is controlled, how food is processed, actions by food preparation personnel, and the like. The controller 18 may output an alert in response to determining that one or more of the food safety compliance rules have been violated. The controller 18 may, for example, be implemented within a local computer and/or within a cloud-based computer.

The alert may enable a supervisor, for example, to better understand deficiencies in employee training. The alert, which may for example be provided to a supervisor or other person via the user interface 16, may include a description of whatever the food safety compliance rule violation was. The alert may include a video clip that illustrates the food safety compliance violation. In some cases, the controller 18 may be configured to perform facial recognition on individuals shown in the video, and the alert may include an identification of an individual causing the food safety compliance violation. In some cases, the alert may be provided in the food area alerting personnel in the food area of the currently occurring food safety compliance violation.

The food safety compliance rules may include a variety of different rules pertaining to the safe handling and storing of food items including perishable or otherwise temperature-sensitive food items. The food safety compliance rules may include one or more rules regarding actions by food preparation personnel. This may include the use of safety equipment, the proper use of gloves, aprons and hair nets, proper hand washing procedures, and the like. The food safety compliance rules may include one or more rules regarding thermal control of food. An example of this includes rules regarding how long particular food items may be kept outside of a target temperature and/or how much the temperature can stray from the target temperature. In some cases, the rules may include one or more rules regarding which food items need to be refrigerated, and thus are to be kept at a temperature below at least 40 degrees Fahrenheit (F). The rules may include one or more rules regarding which food items need to be kept frozen, and thus are to be kept at a temperature below 0 degrees F. The rules may pertain to heated foods ready to serve, and thus may include one or more rules regarding which food items are to be kept at a temperature above 140 degrees F. It will be appreciated that heated foods may need to be cooled for subsequent storage, and thus the rules may include one or more rules regarding how long food items can be between 40 degrees F. and 140 degrees F. when cooling hot food. As an example, some food safety guides specify that a particular food must be cooled from 140 degrees F. down to 70 degrees F. within two hours, and must then be cooled from 70 degrees F. to 40 degrees F. or below within an additional two hours. In some cases, violating part of this cooling time may require the food to be reheated to above 140 degrees F. and then re-cooled in accordance with the guidelines. In some situations, violating the cooling guidelines may require disposal of the food in question.

The food safety compliance rules may, for example, include one or more rules regarding how long food is out of refrigeration while being processed in the food area. The food safety compliance rules may include one or more rules regarding inventory control so as to ensure that food is used on a first in-first out basis. In other words, the oldest is used before the next newest. In some cases, the food safety compliance rules may include one or more rules regarding cross-contamination. This may include rules governing the use of one or more tools and/or food preparation surfaces with one or more first foods while not using the one or more tools and/or food preparation surfaces with one or more second foods without sanitizing the tools and/or food preparation surfaces first. As an example, a knife or cutting board designated for use only with raw meat should not be used when cutting raw vegetables. Cooked meat should not be handled using the same utensils used to put the raw meat into the pan, or on the grill. Cooked meat should not be returned to a plate or basis that previously held the raw meat. These are just a few examples.

In some instances, the video-based food safety compliance system 10 may include one or more sensors 20 that are configured to sense one or more parameters within the food area 12. For example, the video-based food safety compliance system 10 may include one or more temperature sensors for sensing an ambient temperature in the food area 12. The video-based food safety compliance system 10 may include one or more humidity sensors for sensing an ambient temperature within the food area 12.

The food area 12 may generally represent a number of different food areas, that may be temperature controlled or not temperature controlled. As an example, the food area 12 may represent a delivery or inventory receiving area where food deliveries are dropped off. This may include a grocery store back room, where semi-trucks are unloaded, and other deliveries are received. This may include a back room of a restaurant, where perishable and other supplies are brought into the restaurant from one or more delivery trucks. In some cases, the food area 12 may represent a food preparation area of a restaurant, a deli, a grocery store or a butcher shop. These are just examples. In some instances, the food area 12 may represent a food display area such as a salad bar or a heated or cooled buffet table.

Figure 2:
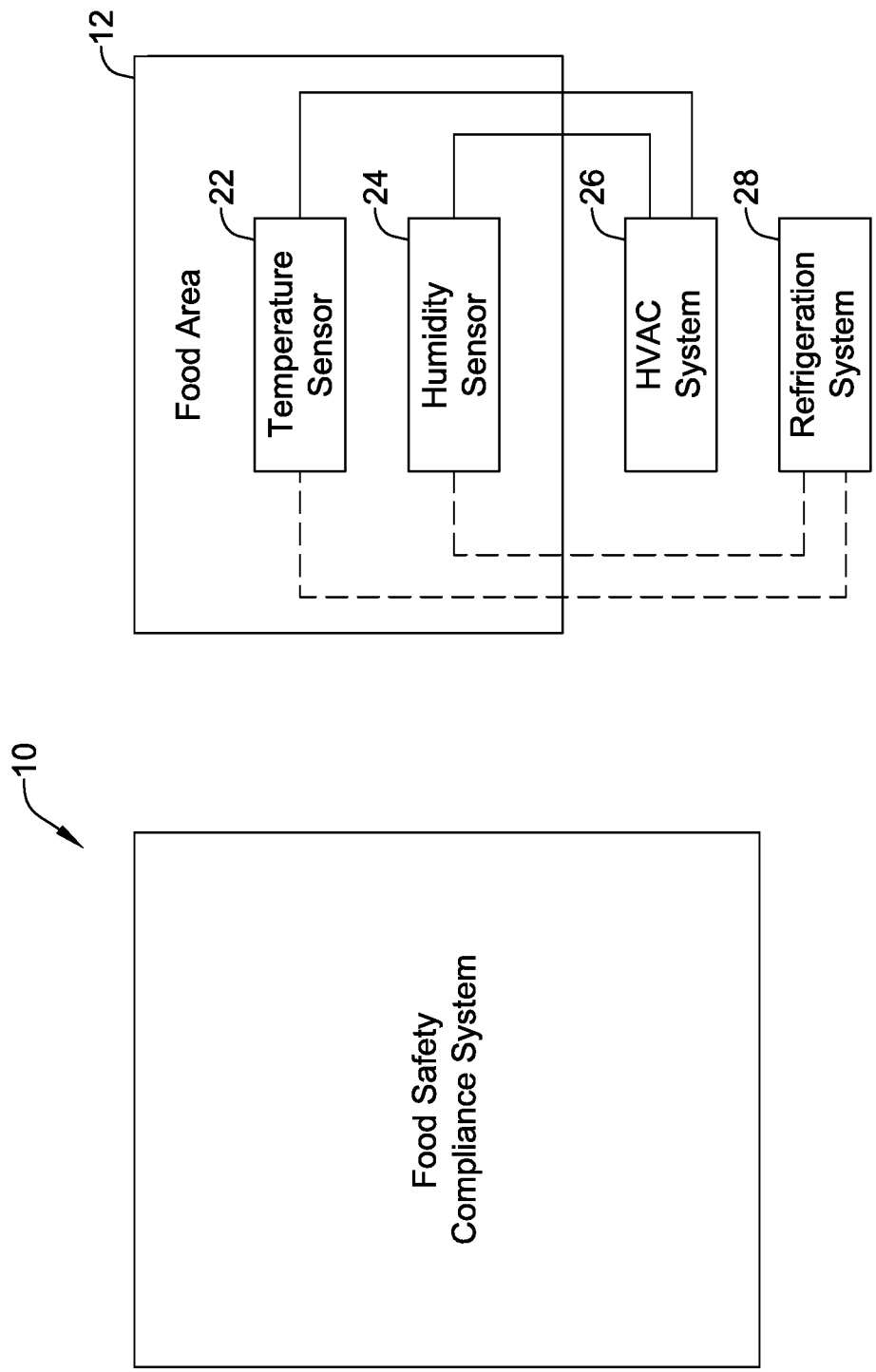
FIG. 2 is a schematic block diagram of the illustrative video-based food safety compliance system of FIG. 1 in use relative to a food area and a Heating, Cooling and Ventilating (HVAC) system.

FIG. 2 is a schematic block diagram showing the illustrative food safety compliance system 10. As shown, the food area 12 may include a temperature sensor 22 that provides a signal indicative of an ambient temperature within the food area 12. The food area 12 may include a humidity sensor 24 that provides a signal indicative of an ambient air temperature within the food area 12. In some cases, the temperature sensor may include an infrared non-contact temperature sensor that is configured to sense the temperature of the food itself in the food areas 12. While a single temperature sensor 22 and a single humidity sensor 24 are shown, it will be appreciated that this is merely illustrative, as the food area 12 may include any number of temperature sensors 22 and/or humidity sensors 24. In some cases, the temperature sensor 22 and/or the humidity sensor 24 may be part of an HVAC system 26 of a building, and the food safety compliance system 10 may be operatively coupled with the HVAC system 26. In some cases, the temperature sensor 22 and/or the humidity sensor 24 may instead be part of a refrigeration system 28 within the building. It will be appreciated that if part of the food area 12 includes a refrigerated section or a frozen section, the refrigeration system 28 may be configured to maintain the refrigerated section at an appropriate temperature below 40 degrees F. and/or to maintain the frozen section at an appropriate temperature below 0 degrees F.

Figure 3:
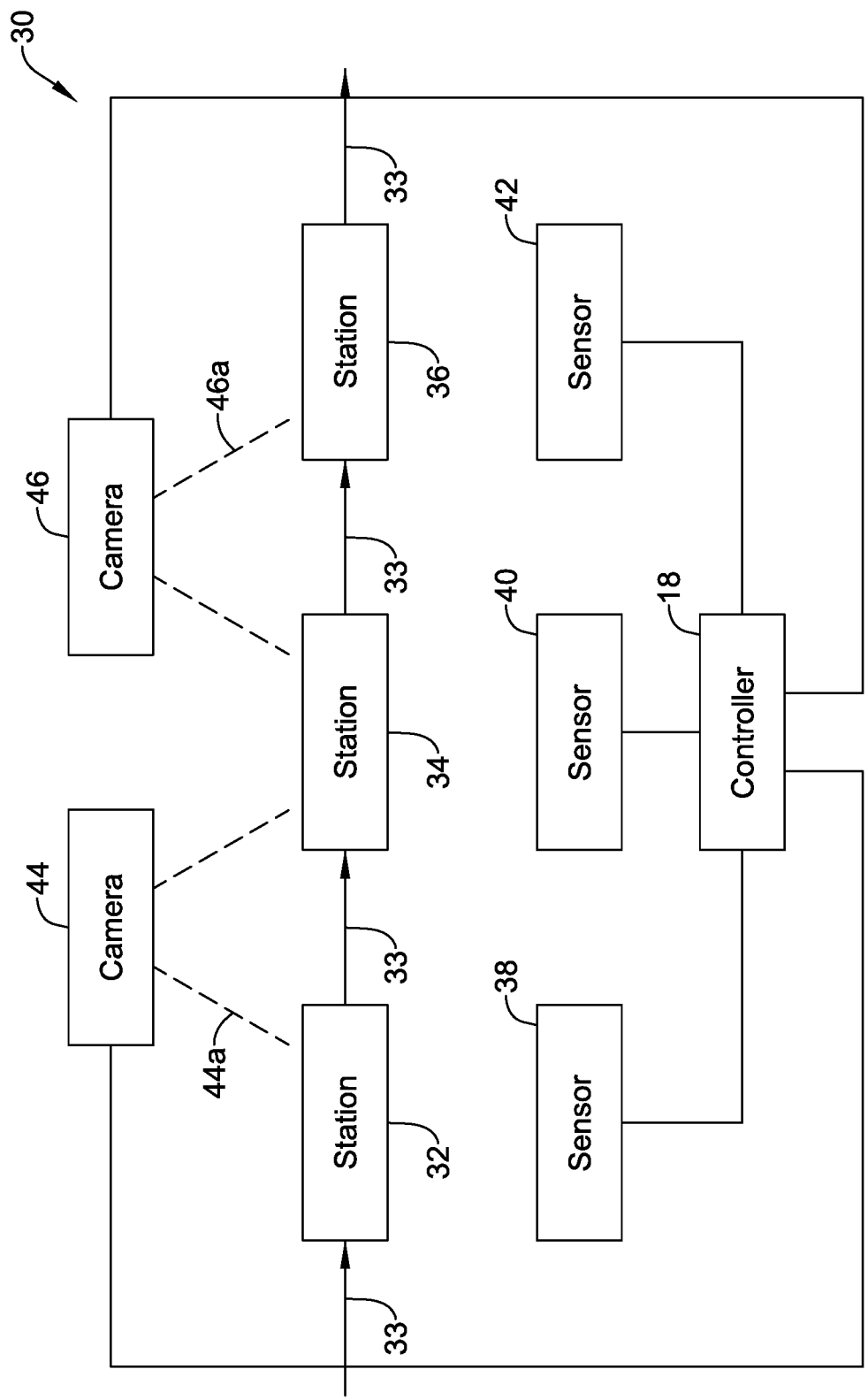
FIG. 3 is a schematic block diagram of an illustrative video-based food safety compliance system in use with a plurality of food preparation stations.

FIG. 3 is a schematic block diagram of a video-based food safety compliance system 30 that may be considered as including any or all of the features described with respect to the video-based food safety compliance system 10 of FIG. 1. Similarly, the video-based food safety compliance system 30 may be considered as including any or all of the features described with respect to the video-based food safety compliance system 10 of FIG. 2. In some cases, the video-based food safety compliance system 30 may be considered as being configured to track a particular food item, through space and time, along a track 33 that includes a station 32, a station 34 and a station 36. Each of the stations 32, 34, 36 may be a food storage area, a food preparation area or a food display area, for example. While a total of three stations 32, 34, 36 are shown, it will be appreciated that in some cases there may be fewer than three stations or there may be four or more distinct stations. The video-based food safety compliance system 30 may include a sensor 38, a sensor 40 and a sensor 42, each of which are operably coupled to the controller 18. While a total of three sensors 38, 40, 42 are shown, it will be appreciated that in some cases there may be fewer than three sensors, or there may be four or more distinct sensors. Each of the sensors 38, 40, 42 may be considered as being configured to sense one or more environmental conditions at and between each of the stations 32, 34, 36. The environmental conditions may include, for example, temperature and/or humidity. While three stations 32, 34, 36 and three sensors 38, 40, 42 are shown, this is merely illustrative, as there may or may not be a one to one pairing of sensor to station.

While not required, in some cases one or more of the sensors 38, 40, 42 may be a non-contact temperature sensor (e.g. Infrared sensor) that is configured to provide an indication of at least a surface temperature of a food item moving between the stations 32, 34, 36. The path that the food item takes between the stations 32, 34, 36 may be considered as being a track 33. The controller 18 may be configured to track a particular food item along the stations 32, 34, 36 in both time and space and to determine, based at least in part on the track 33 and the one or more sensed conditions along the track 33, when one or more food safety compliance rules are violated.

In some cases, the controller 18 may be configured to predict a spoilage time of the particular food item based at least in part on the track 33 and the one or more sensed conditions along the track 33. The track 33 may, for example, begin when the particular food item enters the building. In some cases, the track 33 may end when the particular food item is delivered for consumption. As an example, the track 33 may begin when a perishable food item is received in inventory at a restaurant and may end when the cooked food is presented on a plate to the diner that ordered it. The track 33 may also include only a portion of the journey from inventory to plate.

In some cases, as shown, the video-based food safety compliance system 30 may include a video camera 44 and a video camera 46. There may be only one video camera. In some cases, there may be three, four or more video cameras as needed. The video camera 44 has a field of view 44a and the video camera 46 has a field of view 46a. As illustrated, it can be seen that the field of view 44a includes a portion of the station 34 while the field of view 46a includes a portion of the station 34 and a portion of the station 36. Depending on how many stations there are along the track 33, and how many video cameras there are, it will be appreciated that a food item can be visually tracked from station to station along the track 33.

Figure 4:
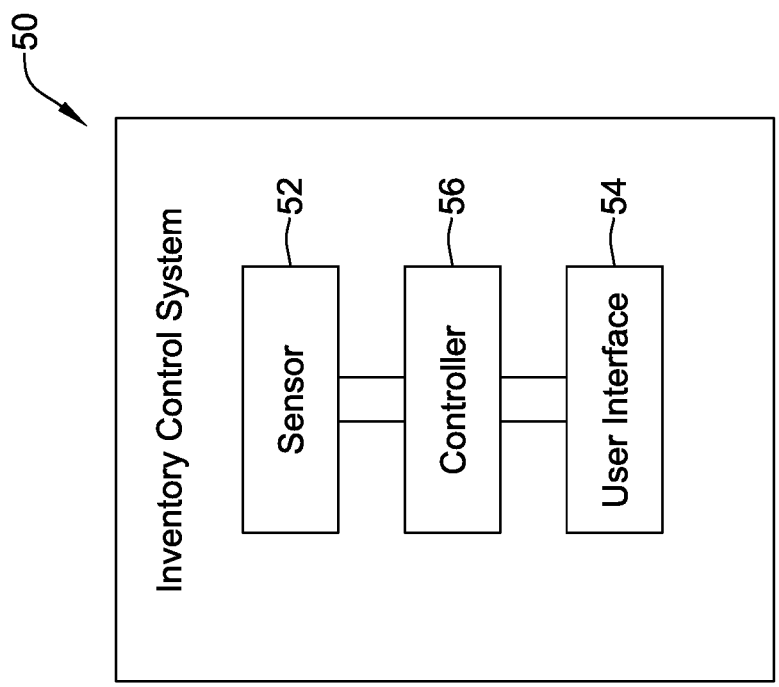
FIG. 4 is a schematic block diagram of an illustrative inventory control system.

FIG. 4 is a schematic block diagram of an illustrative inventory control system 50 for use in controlling food inventory within a food storage area. The food storage area may, for example, be considered as being an example of the food area 12 referenced in FIG. 1. As an example, the food storage area may be a food storage area that is maintained at 40 degrees F. or less. The food storage area may be a food storage area that is maintained at 0 degrees F. or less.

The illustrative inventory control system 50 includes a sensor 52 that is operable to detect a measure of inventory control, a user interface 54 and a controller 56 that is operably coupled to the sensor 52 and to the user interface 54. The controller 56, which may for example include the features of the controller 18, and vice versa, is configured to receive the measure of inventory control from the sensor 52, and to track the measure of inventory control over time. The controller 56 is configured to determine if the measure of inventory control over time, particularly changes in the measure of inventory control over time, indicates a violation of inventory control compliance rules. The controller 56 may be configured to generate a report describing the instances in which inventory control compliance rules are violate and to output the report via the user interface 54 so that a supervisor can implement improvements in compliance with the inventory control compliance rules.

As an example, the sensor 52 may include a code reader, and the measure of inventory control may be a readable code that is placed on an unit of incoming food. A unit of incoming food may be a box or crate of individual food items, or may be a unitary piece of food. The sensor 52 may include a bar code reader, and the measure of inventory control may thus include a bar code. The sensor 52 may include an RF sensor, and the measure of inventory control may include an RFID tag. The sensor 52 may include a camera, and the measure of inventory control may thus include a QR code. As another example, the sensor 52 may be a scale, and the measure of inventory control may include a weight of a food container sitting on and thus being weighed by the scale. The controller 56 may determine an inventory control compliance rule violation if the controller 56 receives an indication that a new food container is used before an existing food container reaches a minimal weight, as an example.

In some cases, the inventory control system 50 may be configured to ensure a first in-first out basis of inventory control. The sensor 52 may include a camera that is configured to provide the controller 56 with one or more images of food items, and the controller 56 may be further configured to analyze the one or more images of food items and provide a measure of inventory control including a predicted life expectancy of the food items. In some cases, the controller 56 may be configured to use the measure of inventory control that includes the predicted life expectancy of the food items to adjust inventory control as would otherwise occur on a first in-first out basis. For example, the inventory control system 50 may providing a listing of food that is reaching the end of its predicted life expectancy, and personnel may then use that food soon to avoid food waste.

Figure 5:
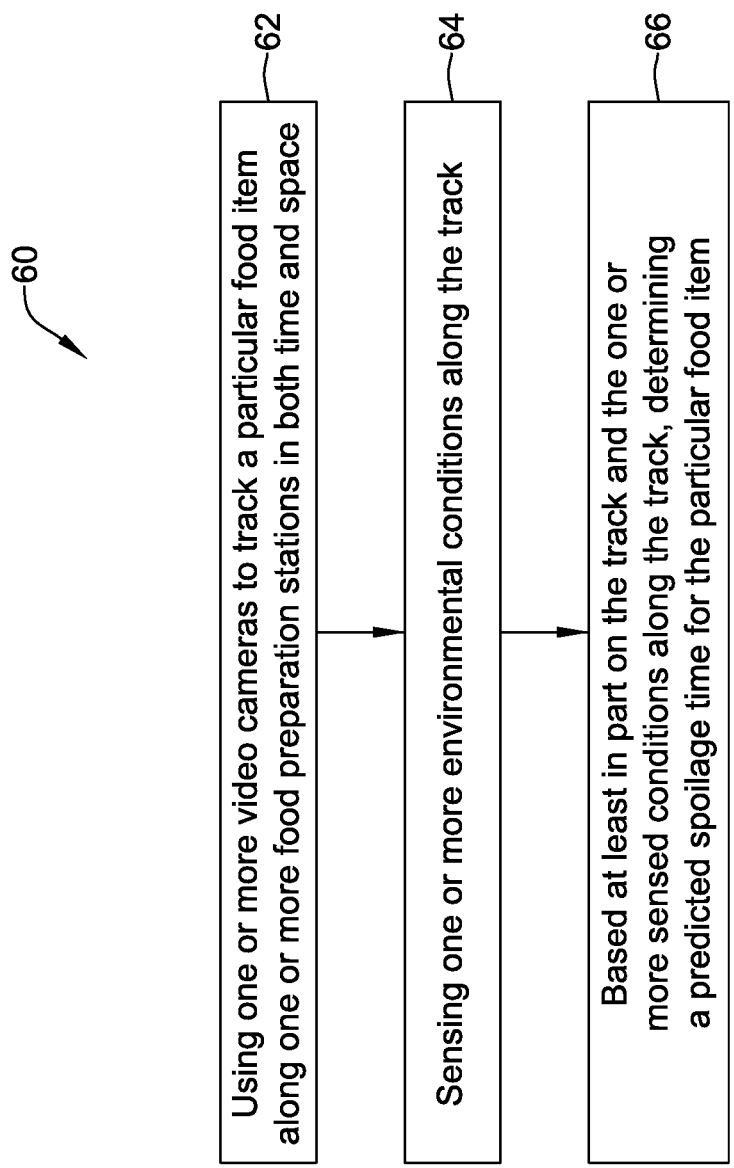
FIG. 5 is a flow diagram showing an illustrative method.

FIG. 5 is a flow diagram of an illustrative method 60 for predicting a spoilage time of a particular food item along a food preparation process in a building. The method includes using one or more video cameras to track a particular food item along a track in both time and space that includes one or more food preparation stations, as indicated at block 62. The food preparation stations may include, for example, one or more a refrigerated storage station, a food preparation station, a food cooking station, and a food staging station. One or more environmental conditions such as but not limited to temperature and/or humidity may be sensed along the track, as indicated at block 64. Based at least in part on the track and the one or more sensed conditions along the track, a predicted spoilage time may be determined for the particular food item, as indicated at block 66. While not required, in some cases, the track begins when the particular food item enters the building. In some cases, the track ends when the particular food item is delivered for consumption.

Figure 6:
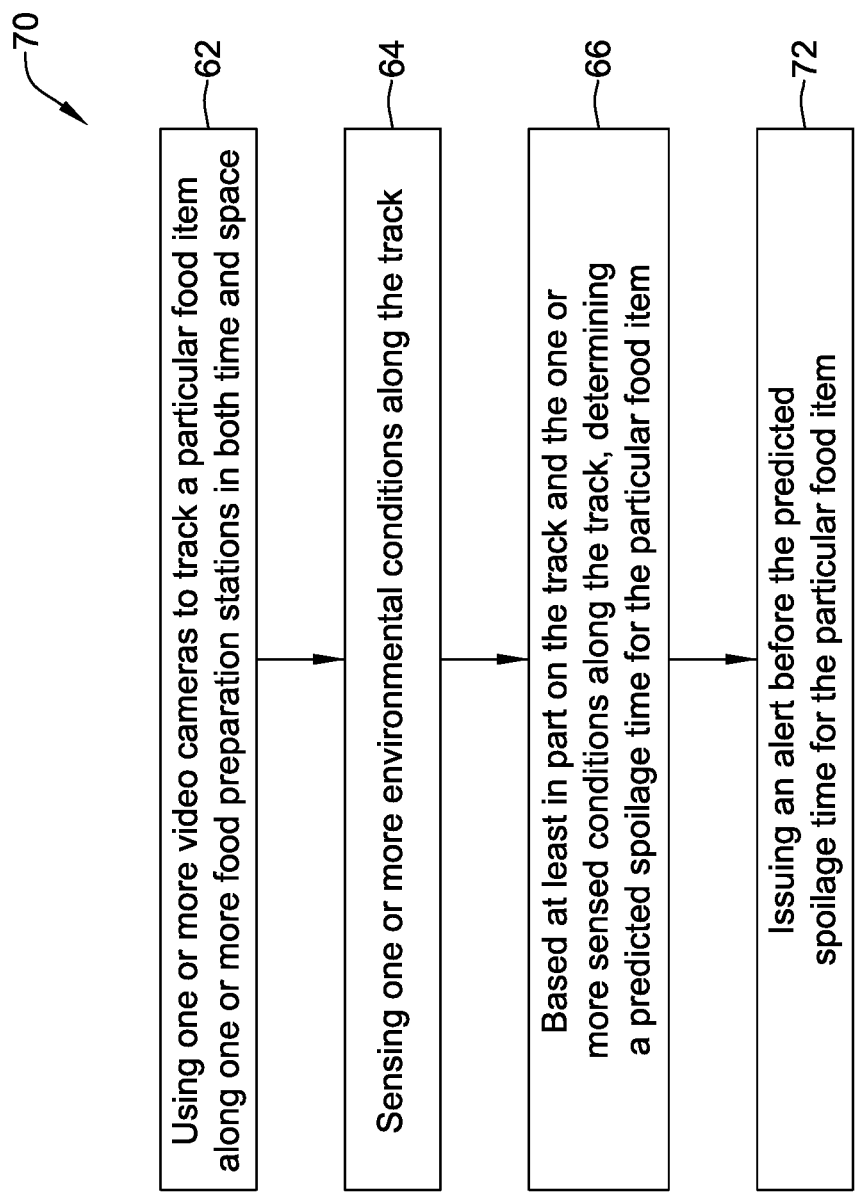
FIG. 6 is a flow diagram showing an illustrative method.

FIG. 6 is a flow diagram of an illustrative method 70 for predicting a spoilage time of a particular food item along a food preparation process in a building. The method includes using one or more video cameras to track a particular food item along a track in both time and space that includes one or more food preparation stations, as indicated at block 62. The food preparation stations may include, for example, one or more a refrigerated storage station, a food preparation station, a food cooking station, and a food staging station. One or more environmental conditions such as but not limited to temperature and/or humidity may be sensed along the track, as indicated at block 64. Based at least in part on the track and the one or more sensed conditions along the track, a predicted spoilage time may be determined for the particular food item, as indicated at block 66. In some cases, and as indicated at block 72, an alert may be issued before the predicted spoilage time for the particular food item. As a result, a decision may be made to dispose of the particular food item, or to take other actions to ensure that it is consumed or otherwise used before the particular food item goes bad.

Figure 7:
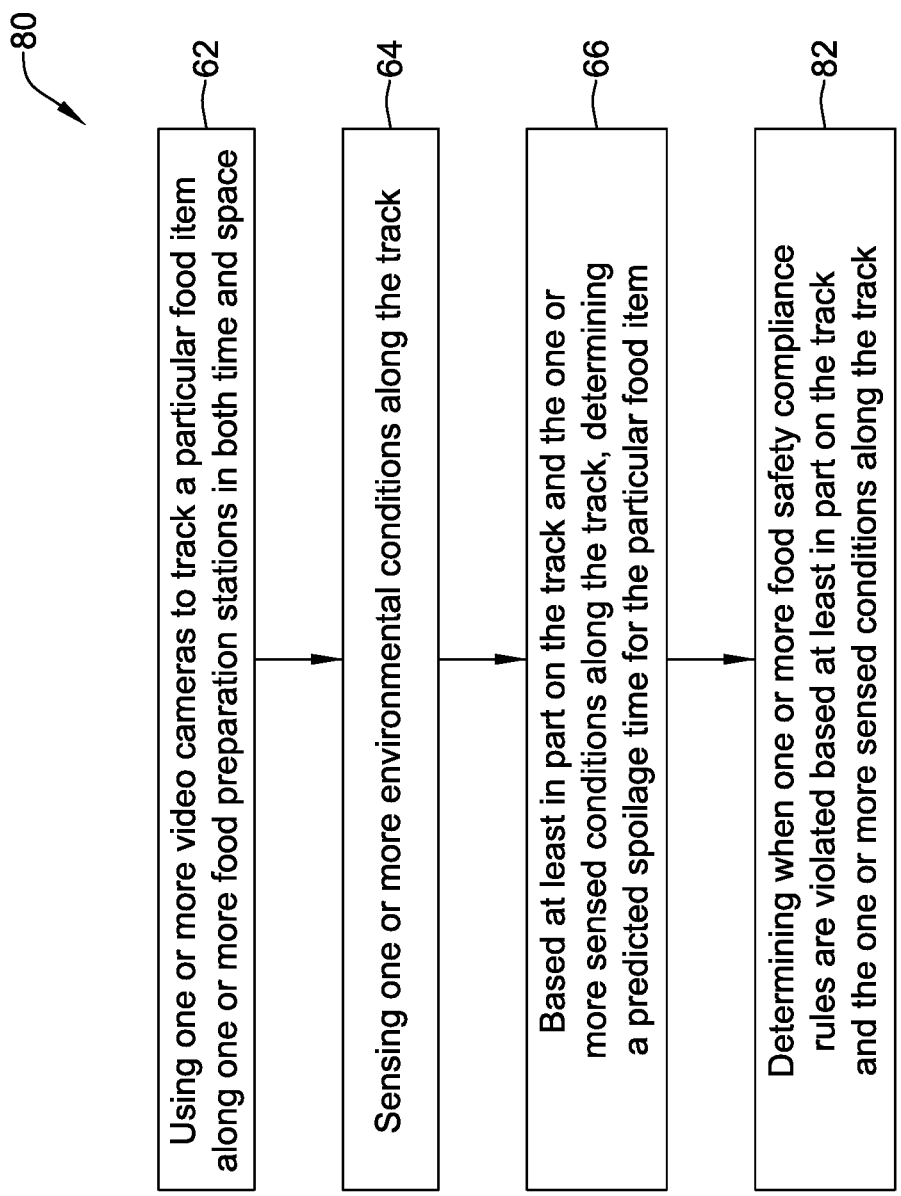
FIG. 7 is a flow diagram showing an illustrative method.

FIG. 7 is a flow diagram of an illustrative method 80 for predicting a spoilage time of a particular food item along a food preparation process in a building. The method includes using one or more video cameras to track a particular food item along a track in both time and space that includes one or more food preparation stations, as indicated at block 62. The food preparation stations may include, for example, one or more a refrigerated storage station, a food preparation station, a food cooking station, and a food staging station. One or more environmental conditions such as but not limited to temperature and/or humidity may be sensed along the track, as indicated at block 64. Based at least in part on the track and the one or more sensed conditions along the track, a predicted spoilage time may be determined for the particular food item, as indicated at block 66. In some cases, a determination may be made that one or more food safety compliance rules are violated based at least in part on the track and the one or more sensed conditions along the track, as indicated at block 82. When use of a food item that has a predicted spoilage time that has already passed is detected, a violation of one or more food safety compliance rules may be determined.

FIG. 8 is a flow diagram of an illustrative method 90 for predicting a spoilage time of a particular food item along a food preparation process in a building. The method includes using one or more video cameras to track a particular food item along a track in both time and space that includes one or more food preparation stations, as indicated at block 62. The food preparation stations may include, for example, one or more a refrigerated storage station, a food preparation station, a food cooking station, and a food staging station. One or more environmental conditions such as but not limited to temperature and/or humidity may be sensed along the track, as indicated at block 64. Based at least in part on the track and the one or more sensed conditions along the track, a predicted spoilage time may be determined for the particular food item, as indicated at block 66. In some cases, as indicated at block 92, a notification may be issued that identifies those particular food items that have a predicted spoilage time that will fall within a threshold period of time (e.g. 1 hour, 2 hours, 1 day, 1 week) from the current time.

Additional Examples

An example of the disclosure includes a video-based food safety compliance system for use in a food area of a building. The video-based food safety compliance system includes a video camera having a field of view that encompasses at least part of the food area, a user interface and a controller that is operably coupled to the video camera and to the user interface. The controller is configured to receive video from the video camera and to analyze the video to determine when one or more food safety compliance rules are violated. The controller outputs an alert in response to determining that one or more of the food safety compliance rules have been violated.

Alternatively or additionally, the video-based food safety compliance system may further include one or more temperature sensors for sensing an ambient temperature in the food area and/or one or more humidity sensors for sensing an ambient humidity in the food area.

Alternatively or additionally, at least one of the one or more temperature sensors and/or one or more humidity sensors may be part of an HVAC system of the building, and the video-based food safety compliance system may be operatively coupled with the HVAC system.

Alternatively or additionally, at least one of the one or more temperature sensors and/or one or more humidity sensors may be part of a refrigeration system of the building.

Alternatively or additionally, the food area may include a delivery area where food deliveries are dropped off.

Alternatively or additionally, the food area may include a food preparation area of a restaurant, a deli, a grocery store or a butcher shop.

Alternatively or additionally, the food area may include a food display area.

Alternatively or additionally, the food display area may include a salad bar or a buffet.

Alternatively or additionally, the video-based food safety compliance system may further include one or more sensors that are operatively coupled to the controller. The controller may be configured to track a particular food item along one or more food preparation stations in both time and space, to sense one or more environmental conditions along the track and, based at least in part on the track and the one or more sensed conditions along the track, determine when one or more food safety compliance rules are violated.

Alternatively or additionally, the one or more sensed conditions may include one or more of temperature and humidity.

Alternatively or additionally, the one or more sensed conditions may include a temperature of the food itself, and the one or more sensors may include an infrared non-contact temperature sensor that is configured to sense the temperature of the food itself.

Alternatively or additionally, the field of view of the video camera may capture at least part of a first one of the food preparation stations.

Alternatively or additionally, the video-based food safety compliance system may further include a second video camera that is operatively coupled to the controller and that has a field of view that captures at least part of a second one or more of the food preparation stations.

Alternatively or additionally, the controller may be configured to predict a spoilage time of the particular food item based at least in part on the track and the one or more sensed conditions along the track.

Alternatively or additionally, the track may begin when the particular food item enters the building.

Alternatively or additionally, the track may end when the particular food item is delivered for consumption.

Alternatively or additionally, the alert may include a description of the food safety compliance rule violation.

Alternatively or additionally, the alert may include a video clip illustrating the food safety compliance violation.

Alternatively or additionally, the controller may be further configured to perform facial recognition on individuals shown in the video, and the alert may include an identification of an individual causing the food safety compliance violation.

Alternatively or additionally, the food safety compliance rules may include one or more rules regarding actions by food preparation personnel.

Alternatively or additionally, the food safety compliance rules may include one or more rules regarding thermal control of food.

Alternatively or additionally, the food safety compliance rules may include one or more rules regarding how long particular food items may be kept outside of a target temperature and/or how much the temperature can stray from the target temperature.

Alternatively or additionally, the one or more rules regarding thermal control may include one or more rules regarding which food items are to be kept at a temperature below at least 40 degrees Fahrenheit (F).

Alternatively or additionally, the one or more rules regarding thermal control may include one or more rules regarding which food items are to be kept at a temperature below 0 degrees F.

Alternatively or additionally, the one or more rules regarding thermal control may include one or more rules regarding which food items are to be kept at a temperature above 140 degrees F.

Alternatively or additionally, the one or more rules regarding thermal control may include one or more rules regarding how long food items can be between 40 degrees F. and 140 degrees F. when cooling hot food.

Alternatively or additionally, the food safety compliance rules may include one or more rules regarding how long food can be out of refrigeration while being processed in the food area.

Alternatively or additionally, the food safety compliance rules may include one or more rules regarding inventory control.

Alternatively or additionally, inventory control may include ensuring that food is used on a first in-first out basis.

Alternatively or additionally, the food area may include an inventory receiving area.

Alternatively or additionally, the inventory receiving area may include an inventory receiving area of a restaurant or a grocery store.

Alternatively or additionally, the food safety compliance rules may include one or more rules regarding cross-contamination.

Alternatively or additionally, the one or more rules regarding cross-contamination may include rules governing the use of one or more tools with one or more first foods while not using the one or more tools with one or more second foods.

Alternatively or additionally, the controller may be implemented within a local computer.

Alternatively or additionally, the controller may be implemented within a cloud-based computer.

Another example of the disclosure includes a method for predicting a spoilage time of a particular food item along a food preparation process in a building. The method includes using one or more video cameras to track a particular food item along one or more food preparation stations in both time and space. One or more environmental conditions are sensed along the track. Based at least in part on the track and the one or more sensed conditions along the track, a predicted spoilage time for the particular food item may be determined.

Alternatively or additionally, the track may begin when the particular food item enters the building.

Alternatively or additionally, the track may end when the particular food item is delivered for consumption.

Alternatively or additionally, one of the one or more food preparation stations may include one or more a refrigerated storage station, a food preparation station, a food cooking station, and a food staging station.

Alternatively or additionally, the method may further include issuing an alert before the predicted spoilage time for the particular food item.

Alternatively or additionally, the method may further include determining when one or more food safety compliance rules are violated based at least in part on the track and the one or more sensed conditions along the track.

Alternatively or additionally, one or more food safety compliance rules may include whether to continue to prepare food at one or more of the food preparation stations that has a predicted spoilage time that has expired.

Alternatively or additionally, the one or more sensed conditions may include on or more of temperature and humidity.

Alternatively or additionally, the method may further include issuing an notification that identifies those particular food items that have a predicted spoilage time that will fall within a threshold period of time (e.g. 1 hour, 2 hours, 1 day, 1 week) from the current time.

Another example of the disclosure includes an inventory control system for use in controlling food inventory within a food storage area. The inventory control system includes a sensor operable to detect a measure of inventory control, a user interface and a controller that is operably coupled to the sensor and to the user interface. The controller is configured to receive the measure of inventory control from the sensor and to track the measure of inventory control over time. The controller is configured to determine if the measure of inventory control over time indicates a violation of inventory control compliance rules. The controller is configured to generate a report describing the instances in which inventory control compliance rules are violated and to output the report via the user interface so that a supervisor can implement improvements in compliance with the inventory control compliance rules.

Alternatively or additionally, the sensor may include a code reader and the measure of inventory control may include a readable code placed on a unit of incoming food.

Alternatively or additionally, the sensor may include a bar code reader and the measure of inventory control may include a bar code.

Alternatively or additionally, the sensor may include a camera and the measure of inventory control may include a QR code.

Alternatively or additionally, the unit of incoming food may include a box, carton or crate of food including a plurality of individual food items.

Alternatively or additionally, the unit of incoming food may include a single food item.

Alternatively or additionally, the sensor may include a scale and the measure of inventory control may include a weight of a food container being weighed by the scale.

Alternatively or additionally, the controller may determine an inventory control compliance issue if the controller receives an indication that a new food container is used before an existing food container reaches a minimal weight.

Alternatively or additionally, the food storage area may include a food storage area maintained at 40 degrees F. or less.

Alternatively or additionally, the food storage area may include a food storage area maintained at 0 degrees F. or less.

Alternatively or additionally, the inventory control system may be configured to ensure a first in-first out basis of inventory control.

Alternatively or additionally, the sensor may be a camera configured to provide the controller with one or more images of food items, and the controller may be further configured to analyze the one or more images of food items and provide a measure of inventory control comprising a predicted life expectancy of the food items.

Alternatively or additionally, the controller may be configured to use the measure of inventory control including the predicted life expectancy of the food items to adjust inventory control as would otherwise occur on a first in-first out basis.

Having thus described several illustrative embodiments of the present disclosure, those of skill in the art will readily appreciate that yet other embodiments may be made and used within the scope of the claims hereto attached. It will be understood, however, that this disclosure is, in many respects, only illustrative. Changes may be made in details, particularly in matters of shape, size, arrangement of parts, and exclusion and order of steps, without exceeding the scope of the disclosure. The disclosure's scope is, of course, defined in the language in which the appended claims are expressed.

What is claimed is:

1. A video-based food safety compliance system for use in a food area of a building, comprising:
   a video camera having a field of view that encompasses at least part of the food area;
   one or more temperature sensors;
   a user interface; and
   a controller operably coupled to the one or more sensors, the video camera and the user interface, the controller configured to:
   receive video captured by the video camera;
   analyze the video to determine when one or more food safety compliance rules are violated by an individual in the food area, wherein the one or more food safety compliance rules include;
   one or more food safety compliance rules regarding use of food safety equipment including proper use of one or more of gloves, aprons and hair nets by the individual in the food area;
   receive a temperature of a heated food in the food area using the one or more temperature sensors;
   analyze the temperature of the heated food over time to determine when one or more food safety compliance rules are violated, wherein the one or more food safety compliance rules include:
   one or more food safety compliance rules that require at least a minimum rate of cooling of the heated food before subsequent storage of the food;
   in response to determining that one or more of the food safety compliance rules have been violated,
   outputting an alert wherein the alert includes a description of the violation.

2. The video-based food safety compliance system of claim 1, further comprising one or more humidity sensors for sensing a humidity in the food area.

3. The video-based food safety compliance system of claim 1, wherein at least one of the one or more temperature sensors includes an infrared non-contact temperature sensor.

4. The video-based food safety compliance system of claim 1, wherein the one or more food safety compliance rules that require at least a minimum rate of cooling of the heated food before subsequent storage require the heated food to be cooled from a first temperature down to a second temperature at a first rate of cooling, and then must be subsequently cooled from the second temperature down to a third temperature at a second rate of cooling, wherein the first rate of cooling is greater than the second rate of cooling.

5. The video-based food safety compliance system of claim 1, wherein the controller is configured to:
   track a particular food item along a track that includes one or more food preparation stations in both time and space;
   sense the temperature along the track; and
   based at least in part on the track and/or the sensed temperature along the track, determine when one or more food safety compliance rules are violated.

6. The video-based food safety compliance system of claim 5, wherein the field of view of the video camera captures at least part of a first one of the food preparation stations.

7. The video-based food safety compliance system of claim 6, further comprising a second video camera operatively coupled to the controller, wherein the second video camera has a field of view that captures at least part of a second one or more of the food preparation stations.

8. The video-based food safety compliance system of claim 1, wherein the alert includes an identification of the particular individual causing the violation of one or more of the food safety compliance rules.

9. The video-based food safety compliance system of claim 1, wherein the food safety compliance rules include:
   one or more rules regarding food handling; and
   one or more rules regarding thermal control of food.

10. The video-based food safety compliance system of claim 1, wherein the food safety compliance rules include one or more rules regarding use of proper hand washing procedures by the individual.

11. The video-based food safety compliance system of claim 1, wherein the food safety compliance rules include one or more rules regarding cross-contamination.

12. A video-based food safety compliance system for use in a food preparation area of a building, comprising:
- a video camera having a field of view that encompasses at least part of the food preparation area;
- one or more temperature sensors;
- a user interface; and
- a controller operably coupled to the one or more temperature sensors, the video camera and the user interface, the controller configured to:
  - receive video from the video camera;
  - analyze the video to determine when one or more food safety compliance rules are violated, wherein one or more food safety compliance rules include one or more rules regarding food handling by an individual;
  - receive a temperature of a heated food in the food preparation area using the one or more temperature sensors;
  - analyze the temperature of the heated food over time to determine when one or more food safety compliance rules are violated, wherein the one or more food safety compliance rules include one or more rules regarding thermal control of food including a rule that requires at least a minimum rate of cooling of the heated food before subsequent storage of the food;
  - in response to determining that one or more food safety compliance rules have been violated:
    - outputting an alert, wherein the alert includes a description of the violation.

13. The video-based food safety compliance system of claim 12, wherein:
- one or more of the one or more food safety compliance rules are violated when one or more tools are used with one or more first foods followed by using the one or more tools with one or more second foods without sanitizing the one or more tools first; and
- the alert includes a video clip captured by the video camera that shows use of one or more tools with one or more first foods followed by using the one or more tools with one or more second foods without sanitizing the one or more tools and/or food preparation surfaces first.

14. The video-based food safety compliance system of claim 12, wherein:
- one or more of the one or more food safety compliance rules are violated when one or more food preparation surfaces are used with one or more first foods followed by using the one or more food preparation surfaces with one or more second foods without sanitizing the one or more food preparation surfaces first; and
- the alert includes a video clip captured by the video camera that shows use of one or more food preparation surfaces with one or more first foods followed by using the one or more food preparation surfaces with one or more second foods without sanitizing the one or more food preparation surfaces first.

15. The video-based food safety compliance system of claim 12, wherein the controller is configured to:
- track a particular food item along a path that includes one or more food preparation stations in both time and space;
- sense the temperature along the path; and
- based at least in part on the path and/or sensed temperature along the path, determine when one or more food safety compliance rules are violated.

16. The video-based food safety compliance system of claim 12, wherein at least one of the one or more temperature sensors includes an infrared non-contact temperature sensor.

17. The video-based food safety compliance system of claim 12, wherein the one or more food safety compliance rules that require at least a minimum rate of cooling of the heated food before subsequent storage require that the heated food be cooled from a first temperature down to a second temperature at a first rate of cooling, and then must be subsequently cooled from the second temperature down to a third temperature at a second rate of cooling, wherein the first rate of cooling is greater than the second rate of cooling.

18. A video-based food safety compliance system for use in a food area of a building, comprising:
- a video camera having a field of view that encompasses at least part of the food area;
- one or more temperature sensors including an infrared non-contact temperature sensor;
- a user interface; and
- a controller operably coupled to the one or more temperature sensors, the video camera and the user interface, the controller configured to:
  - receive video from the video camera;
  - analyze the video to determine when one or more food handling rules are violated by an individual in the food area;
  - receive a temperature of a heated food in the food area using the one or more temperature sensors;
  - analyze the temperature of the heated food over time to determine when one or more food safety compliance rules are violated, wherein the one or more food safety compliance rules include one or more rules regarding thermal control of food including a rule that requires the heated food to be cooled from a first temperature down to a second temperature at a first rate of cooling, and then must be subsequently cooled from the second temperature down to a third temperature at a second rate of cooling, wherein the first rate of cooling is greater than the second rate of cooling;
  - in response to determining that one or more food handling rules are violated,
    - outputting an alert, wherein the alert includes a description of the violation.

19. The video-based food safety compliance system of claim 18, wherein the food handling rules include one or more rules regarding cross-contamination of food.

20. The video-based food safety compliance system of claim 18, wherein the food handling rules include one or more rules regarding use of proper hand washing procedures by the individual.

* * * * *